US010507198B2

(12) United States Patent
Hoffman

(10) Patent No.: US 10,507,198 B2
(45) Date of Patent: *Dec. 17, 2019

(54) PHARMACEUTICAL COMPOSITIONS AND METHODS

(71) Applicant: Tyme, Inc., Wilmington, DE (US)

(72) Inventor: Steven Hoffman, Mahwah, NJ (US)

(73) Assignee: Tyme, Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/298,504

(22) Filed: Mar. 11, 2019

(65) Prior Publication Data
US 2019/0201378 A1 Jul. 4, 2019

Related U.S. Application Data

(63) Continuation of application No. 15/351,966, filed on Nov. 15, 2016, which is a continuation-in-part of application No. 14/750,877, filed on Jun. 25, 2015, now Pat. No. 9,549,969, which is a continuation of application No. 13/742,865, filed on Jan. 16, 2013, now abandoned, which is a continuation-in-part of application No. 13/371,076, filed on Feb. 10, 2012, now Pat. No. 8,481,498.

(60) Provisional application No. 61/702,994, filed on Sep. 19, 2012, provisional application No. 61/587,420, filed on Jan. 17, 2012.

(51) Int. Cl.
A61K 38/00 (2006.01)
A61P 35/00 (2006.01)
A61K 31/404 (2006.01)
A61K 31/198 (2006.01)
A61K 31/4166 (2006.01)
A61K 31/436 (2006.01)
A61K 38/12 (2006.01)
A61K 31/19 (2006.01)
A61K 31/366 (2006.01)
A61K 31/55 (2006.01)
A61K 31/787 (2006.01)
A61K 38/31 (2006.01)
A61K 9/48 (2006.01)
A61K 9/00 (2006.01)

(52) U.S. Cl.
CPC ............ A61K 31/404 (2013.01); A61K 31/19 (2013.01); A61K 31/198 (2013.01); A61K 31/366 (2013.01); A61K 31/4166 (2013.01); A61K 31/436 (2013.01); A61K 31/55 (2013.01); A61K 31/787 (2013.01); A61K 38/12 (2013.01); A61K 38/31 (2013.01); A61K 9/0019 (2013.01); A61K 9/48 (2013.01)

(58) Field of Classification Search
None
See application file for complete search history.

(56) References Cited

U.S. PATENT DOCUMENTS

| | | |
|---|---|---|
| 4,117,161 A | 9/1978 | Pozuelo |
| 4,165,382 A | 8/1979 | Pozuelo |
| 4,189,604 A | 2/1980 | Umezawa et al. |
| 4,240,975 A | 12/1980 | Umezawa et al. |
| 4,389,415 A | 6/1983 | Scriabine |
| 4,389,416 A | 6/1983 | Plattner |
| 5,073,541 A | 12/1991 | Taylor et al. |
| 5,206,018 A | 4/1993 | Sehgal et al. |
| 5,225,435 A | 7/1993 | Pawelek et al. |
| 5,310,539 A | 5/1994 | Williams |
| 5,576,290 A | 11/1996 | Hadley |
| 5,674,839 A | 10/1997 | Hruby et al. |
| 5,683,981 A | 11/1997 | Hadley et al. |
| 5,714,576 A | 2/1998 | Hruby et al. |
| 6,359,001 B1 | 3/2002 | Drago |
| 7,452,868 B2 | 11/2008 | Kuzma et al. |
| 8,481,498 B1 * | 7/2013 | Hoffman ................ A61K 38/34 514/19.2 |
| 9,549,969 B2 * | 1/2017 | Hoffman ................ A61K 38/12 |
| 9,895,425 B2 * | 2/2018 | Hoffman ................ A61K 38/12 |
| 10,010,590 B2 * | 7/2018 | Hoffman ................ A61K 38/12 |
| 2002/0128304 A1 | 9/2002 | D'Amato |
| 2003/0059471 A1 | 3/2003 | Compton et al. |
| 2003/0232767 A1 | 12/2003 | Agrawal et al. |
| 2005/0165301 A1 | 7/2005 | Smith et al. |
| 2006/0024365 A1 | 2/2006 | Vaya et al. |
| 2006/0063699 A1 | 3/2006 | Larsen |
| 2009/0030067 A1 | 1/2009 | Wosikowski-Buters et al. |
| 2009/0142337 A1 | 6/2009 | Squires |
| 2010/0104660 A1 | 4/2010 | Yu |
| 2010/0216781 A1 | 8/2010 | Perrin-Ninkovic et al. |
| 2013/0183263 A1 | 7/2013 | Hoffman |

FOREIGN PATENT DOCUMENTS

| CN | 1255064 A | 5/2000 |
|---|---|---|
| CN | 101045041 A | 10/2007 |

(Continued)

OTHER PUBLICATIONS

Brogden, R.N., et al., "α-Methyl-p-Tyrosine: A review of its Pharmacology and Clinical Use," Drugs 21:81-89 (1981) (Year: 1981).*

(Continued)

Primary Examiner — Julie Ha
Assistant Examiner — Kristina M Hellman
(74) Attorney, Agent, or Firm — BakerHostetler

(57) ABSTRACT

Pharmaceutical compositions and kits including a tyrosine hydroxylase inhibitor; melanin, a melanin promoter, or a combination thereof; a p450 3A4 promoter; and a leucine aminopeptidase inhibitor are provided. Also provided are methods of treating cancer in a subject, comprising administering an effective amount of a tyrosine hydroxylase inhibitor, a melanin promoter, a p450 3A4 promoter, and a leucine aminopeptidase inhibitor to the subject in need thereof. Also provided are methods of reducing cell proliferation in a subject comprising administering an effective amount of a tyrosine hydroxylase inhibitor, a melanin promoter, a p450 3A4 promoter, and a leucine aminopeptidase inhibitor to the subject in need thereof.

4 Claims, No Drawings

(56) References Cited

FOREIGN PATENT DOCUMENTS

| | | |
|---|---|---|
| DE | 3823735 A1 | 3/1989 |
| EP | 1582207 A1 | 10/2005 |
| JP | 2-502022 A | 7/1990 |
| WO | 89/04666 A1 | 6/1989 |
| WO | 9410968 A1 | 5/1994 |
| WO | 9847515 A1 | 10/1998 |
| WO | 2002100885 A2 | 12/2002 |
| WO | 2005072061 A2 | 8/2005 |
| WO | 2008027837 A2 | 3/2008 |
| WO | 2009033712 A2 | 3/2009 |
| WO | 2009054001 A1 | 4/2009 |
| WO | 2009109649 A1 | 9/2009 |
| WO | 2009131631 A1 | 10/2009 |
| WO | 2010022243 A1 | 2/2010 |
| WO | 2010118419 A2 | 10/2010 |
| WO | 2011112576 A1 | 9/2011 |
| WO | 2011129765 A1 | 10/2011 |
| WO | 2013109610 A1 | 7/2013 |
| WO | 2016105530 A1 | 6/2016 |

OTHER PUBLICATIONS

Landmark, C.J., "Antiepileptic Drugs in Non-Epilepsy Disorders—Relations between Mechanisms of Action and Clinical Efficacy," CNS Drugs 22:27-47 (2008) (Year: 2008).*

Ryakhovsky, V.V., et al., "The first preparative solution phase synthesis of melanotan II," Beilstein Journal of Organic Chemistry 4:1-6 (2008) (Year: 2008).*

Terauchi, M., et al., "Inhibition of APN/CD13 leads to suppressed progressive potential in ovarian carcinoma cells," BMC Cancer 7:1-12 (2007) (Year: 2007).*

Morgan et al., "Local treatment of metastatic cancer—killing the seed or disturbing the soil?," Nat. Rev. 8:504-506 (Aug. 2011) (Year: 2011).*

National Institute of Cancer—understanding and related topics, accessed Aug. 21, 2014 at URL: cancer.gov/canertopics/understandingcancer, 63 pages.

Merck Manuals Lung Carcinoma accessed Mar. 12, 2017 at URL merckmanuals.com/professional/pulmonary-disorders/tumors-of-the-lungs/lun- g-carcinoma, 18 pages.

Merck Manuals Neuroblastoma accessed Mar. 12, 2017 at URL merckmanuals.com/professional/ pediatrics/pediatric-cancers/neuroblastoma, 4 pages.

Cholangiocarcinoma accessed Mar. 12, 2017 at URL surgery.usc.edu/divisions/tumor/pancreasdiseases/web%20pages/BILIARY%20SY- STEM/cholangiocarcinoma, 2 pages.

Thyroid cancers accessed Mar. 12, 2017 at URL www.merckmanuals.com/professional/endocrine-and-metabolic-disorders/thyro- id-disorders/thyroid-cancers, 4 pages.

Merck Manual Colorectal Cancer accessed Aug. 21, 2014 at URL merckmanuals.com/home/digestive_disorders/tumors_of_the_digestive_system/- colorectal_cancer.htm, 5 pages.

Merck Manual Prostate Cancer accessed Aug. 21, 2014 at URL: merckmanuals.com/home/kidney_and_urinary_tract_disorders/cancers_of_the_k- idney_and_genitourinary_tract/prostate_cancer.html?qt=prostate cancer&alt=sh, 8 pages.

Renal cell carcinoma, accessed Mar. 12, 2017 at URL merckmanuals.com/professional/genitourinary-disorders/genitourinary-cance- r/renal-cell-carcinoma, 6 pages.

Hoffman et al., "An open-label trial of SMK treatment of advanced metastatic cancer", 18.sup.th World Congress on Controversies in Obstetrics, Gynecology & Infertility (COGI), Oct. 24-27, 2013, 8 pages.

Patchell, "The management of brain metastases," Cancer Treatment Rev. 29:533-540 (2003).

Fidler, "The pathogenesis of cancer metastasis: the 'seed and soil' hypothesis revisited," Nat. Rev. 3:1-6 (2003).

Bagi, "Targeting of therapeutic agents to bone to treat metastatic cancer," Adv. Drug Deliv. Rev. 57:995-1010 (2005).

Bhatia, "Treatment of Metastatic Melanoma: An Overview," Oncol. 23:488-496 (2009).

Cleveland Clinic (Metastatic Cancer, accessed Apr. 29, 2018 at clevelandclinic.org/health/diseases/17224-metastatic-cancer, pp. 1-4).

Hoffman et al., "SM88/SMK non-hormonal therapy in recurrent or untreated prostate cancer", Journal of Clinical Oncology, 2017, 35, 2017 ASCO Annual Meeting, Suppl.; abstract e16540, 3.

Bergman et al., "The EORTC QLC-LC13: a modular supplement to the EORTC Core Quality of Life Questionnaire (QLQ-C30) for use in lung cancer clinical trials", EORTC Sudy Group on Quality of Life, Eur. J. Cancer, 1994, 30A(5), 635-642.

Boni et al., "Radioiodine-labelled alpha-methyl-tyrosine in malignant melanoma: cell culture studies and results in patients", British Journal of Dermatology, Jul. 1997, vol. 137, Issue 1, 96-100.

Taveria-DaSilva, "Sirolimus therapy in patients with lymphangioleiomyomatosis", Summaries for patients, Annals of Internal Medicine, Jun. 21, 2011, 154(12), I44.

Cabrera Lopez et al., "Effects of rapamycin on angiomyolipomas in patients with tuberous sclerosis", Nefrologia, Apr. 2011, 31(3), 292-298.

Chemwatch, ".alpha.-Methyl-DL-tyrosine", Material Safety Data Sheet, Mar. 11, 2011, 1-7.

Chembase.cn, ".alpha.-Methyl-L-tyrosine", http:en.chembase.cn/substance-349924.html, Feb. 7, 2014, 2 pages.

Chen, "Progress in the development of bestatin analogues as aminopeptidases inhibitors", Current Medical Chemistry, Mar. 2011, vol. 18, No. 7, 964-976.

Chhun et al., "7. The Cytochrome P-450 2C9/2C19 but Not the ABCB1 Genetic Polymorphism May Be Associated With the Liver Cytochrome 3A4 Induction by Phenytoin", Journal of Clinical Psychopharmacology, Jun. 2012, vol. 32, No. 3, 429-431.

Hoffman et al., "SMK/SM88 toxicity, efficacy, and patient reported outcomes in metastatic pancreas cancer", Journal of Clinical Oncology, 2017, 35, 2017 ASCO Annual Meeting, Suppl.; abstract e14060, 1 page.

Dorr et al., "Evaluation of melanotan-II, a superpotent cyclic melanotropic peptide in a pilot phase-I clinical study", Life Sciences, Apr. 1996, vol. 58, Issue 20, 1777-1784.

Ell, "Brain tumor uptake of iodo-alpha-methyl-tyrosine", Journal of Nuclear Medicine, Nov. 1991, 32(11), 2193-2194.

Espeillac et al., "S6 kinase 1 is required for rapamycin-sensitive liver proliferation after mouse hepatectomy", The Journal of Clinical Investigation, Jul. 2011, 121(7), 2821-2832.

Ewa Chodurek et al., "Evaluation of melanogenesis in A-375 melanoma cells treated with 5,7-dimethoxycoumarin and valproic acid", Cellular & Molecular Biology letters: An International Journal, Sep. 20, 2012, vol. 17, No. 4, 616-632.

Fan et al., "Impact of system L amino acid transporter 1 (LAT1) on proliferation of human ovarian cancer cells: a possible target for combination therapy with anti-proliferative aminopeptidase inhibitors", Biochemical Pharmacology, Sep. 15, 2010, vol. 80, Issue 6, 811-818.

Fitzgerald et al., "Effect of Melanotan, [Nle(4), D-Phe(7)]-alpha-MSH, on melanin synthesis in humans with MC1R variant alleles", Peptides, Feb. 2006, vol. 27, Issue 2, 388-394.

Ichimura et al., "Immunohistochemical expression of aminopeptidase N (CD13) in human lung squamous cell carcinomas, with special reference to Bestatin adjuvant therapy", Pathology International, Jun. 2006, vol. 56, Issue 6, 296-300.

Kargiotis et al., "Epilepsy in the cancer patient", Cancer Chemotherapy and Pharmacology, Mar. 2011, vol. 67, No. 3, 489-501.

Krige et al., "CHR-2797: An antiproliferative aminopeptidase inhibitor that leads to amino acid deprivation in human leukemic cells", Cancer Research, Aug. 15, 2008, 68(16), 6669-6679.

Kulke et al., "Future directions in the treatment of neuroendocrine tumors: consensus report of the National Cancer Institute Neuroendocrine Tumor clinical trials planning meeting", Journal of Clinical Oncology, Mar. 2011, vol. 29, No. 1, 934-943.

Tada, "Three cases of malignant pheochromocytoma treated with cyclophosphamide, vincristine, and dacarbazine combination chemotherapy and alpha-methyl-p-tyrosine to control hypercatecholaminemia", Hormone Research, Jan. 1998, vol. 49, No. 6, 295-297.

(56) References Cited

OTHER PUBLICATIONS

Law et al., "Rapamycin: An anti-cancer Immunosuppressant?", Critical Reviews in Oncology/Hematology, Oct. 1, 2005, vol. 56, No. 1, 47-60.
Longo et al., "Efficacy and tolerability of long-acting octreotide in the treatment of thymic tumors: results of a pilot trial", American Journal of Clinical Oncology, Apr. 2012, 35(2), 105-109.
Nakagami, "A case of malignant pheochromocytoma treated with 131I-metaiodobenzylguanidine and alpha-methyl-p-tyrosine", Japanese Journal of Medicine, May-Jun. 1990, vol. 29, No. 3, 329-333.
Oken et al., Toxicity and Response Criteria of the Eastern Cooperative Oncology Group, American Journal of Clinical Oncology, Dec. 1982, 5, 649-655.
Ram et al., "Failure of alpha-methyltyrosine to prevent hypertensive crisis in pheochromocytoma", Archives of Internal Medicine, Nov. 1985, vol. 145, No. 11, 2114-2115.
Steinsapir et al., "Metyrosine and pheochromocytoma", Archives of Internal Medicine, Apr. 1997, vol. 157, No. 8, 901-906.
Tsukamoto et al., "Aminopeptidase N (APN)/CD13 inhibitor, Ubenimex, enhances radiation sensitivity in human cervical cancer", BMC Cancer, Mar. 2008, 8:74, 8 pages.
Voorhess, "Effect of alpha-methyl-p-tyrosine on 3,4-dihydroxyphenylalanine (DOPA) excretion of hamsters with melanotic melanoma", Cancer Research, Mar. 1968, 28, 452-454.
Zimmermann et al., "Prolonged Inhibition of Presynaptic Catecholamine Synthesis With .alpha.-Methyl-Para-Tyrosine Attenuates the Circadian Rhythm of Human TSH Secretion" J. Soc. Gynecol Investing, May/Jun. 2001, vol. 8 No. 3, 174-178.
Del Priore et al., "Phase Ib/II, open-label, dose escalation study to evaluate the safety, pharmacokinetics, and efficacy of SM88 in patients with prostate cancer", Journal of Clinical Oncology, 2017, 35, 2017 ASCO Annual Meeting, Suppl.; abstract TPS2615, 2 pages.
Del Priore et al., "SM88 in non-metastatic rising PSA-recurrent prostate cancer", Journal of Clinical Oncology, 2017, 35, 2017 ASCO Annual Meeting, Suppl.; abstract e16567, 2 pages.
Hoffman et al., "An open-label trial of SMK treatment of advanced metastatic cancer", Journal of Clinical Oncology, 2013, 31, 2013 ASCO Annual Meeting, Suppl.; abstract e22095, 1 page.
Hoffman, et al., SM-88 Therapy in Patients with Advanced or Metastatic Pancreatic Cancer, Poster Presentation, 2018 American Society of Clinical Oncology (ASCO) Gastrointestinal Cancers Symposium in San Francisco, CA; Jan. 19, 2018.
Livstone, "Pancreatic Cancer", Merck Manual, https://www.merckmanuals.com/profressional/gastrointestinal-disorders/tum-ors-of-the-gi-tract/pancreatic-cancer, accessed Mar. 12, 2017, 5 pages.
Roste et al., "2.268 Influence of Valproate and Phenytoin Onestrogen-Stimulated Cell Growth in the Humanbreast Cancer Cell Line MCF-7", Epilepsia, Oct. 2002.
Chiu et al., "Lipid-Based Nanoparticulate Systems for the Delivery of Anti-Cancer Drug Cocktails: Implications on Pharmacokinetics and Drug Toxicities", Current Drug Metabolism, 2009, 10, 861-874.
Moreira et al., "A Novel Transdermal Delivery System for the Anti-Inflammatory Lumiracoxib: Influence of Oleic Acid on In Vitro Percutaneous Absorption and In Vivo Potential Cutaneous Irritation" AAPS PharmSciTech, vol. 11, No. 2, Jun. 2010, pp. 621-629.
Chang et al., "Rapamycin Inhibits Proliferation of Estrogen-Receptor-Positive Breast Cancer Cells" Journal of Surgical Research, vol. 138, No. 1, Mar. 2007, pp. 37-44.
Cibmtr. "Lymphoma Response Criteria," Forms Instruction Manual, retrieved from https://www.cibmtr.org/manuals/fim/1/en/topic/lymphoma-response- criteria, accessed on Nov. 2, 2018.
Eisenhauer, E. A. et al. (2009). "New response evaluation criteria in solid tumours: Revised RECIST guideline (version 1.1)," European Journal of Cancer 45: 228-247.
Fraser, S. P. et al. (2003). "Contribution of Functional Voltage-Gated Na.sup.+Channel Expression to Cell Behaviors Involved in the Metastatic Cascade in Rat Prostate Cancer: I. Lateral Motility," Journal of Cellular Physiology 195: 479-487.
Jang, R. W. et al. (Sep. 2014). "Simple Prognostic Model for Patients with Advanced Cancer Based on Performance Status," Journal of Oncology Practice 10(5): e335-e341.
Malalasekera, A. et al. (2016). "Eastern Cooperative Oncology Group score: Agreement between non-small-cell lung cancer patients and their oncologists and clinical implications," Cancer Treatment Communications 5: 17-21.
Onganer, P. U. et al. (2005). "Small-cell Lung Cancer (Human): Potentiation of Endocytic Membrane Activity by Voltage-gated Na.sup.+Channel Expression in Vitro," Journal of Membrane Biology 204: 67-75.
Tyme, Inc. (Jun. 2018). "SM-88 First Human Study (FHS) and Compassionate Use Program Clinical Analysis," 23 pages.
Liu et al., "Combinatorial effects of lapatinib and rapamycin in triple-negative breast cancer cells", Molecular Cancer Therapeutics, Aug. 2011, 10, 1460-1469.
Cancer Treatment Centers of America, "Metastasis", accessed Jul. 19, 2017 at URL cancercenter.com/terms/metastasis, 2 pages.
Okada et al., "A Long Survived Case of Malignant Pheochromocytoma Treated with α-methyl-p-tyrosine and Midaglizol (DG-5128)" J. Jpn. Soc. Cancer Ther. vol. 23, No. 6, Jun. 1990, pp. 1221-1225.
Yamakada, "α-methyl-para-tyrosine in the treatment of malignant Pheochromocytoma" Center for Multiphase Health Testing and Services, vol. 55, 2007, pp. 21-26.
Caplea et al., "Noradrenergic content and turnover rate in kidney and heart shows gender and strain differences" J. Appl. Physiol. vol. 92, 2002, pp. 567-571.
Pyorala et al., ".alpha.-Methyl-p-tyrosine in the symptomatic treatment of patients with malignant pheochromocytoma" Database accession No. 1969: 27538, Annales Medicinae Internae Fenniae, 1968, 57(2), 65-73 Coden: AMFNAE; ISSN: 0365-4362, XP002790305, 1 Page.
Li et al., "Pancreatic Cancer," Lancet 363: 1049-1057 (2004) (Year 2004)[in related U.S. Appl. No. 16/420,900].

\* cited by examiner

PHARMACEUTICAL COMPOSITIONS AND METHODS

CROSS-REFERENCE TO RELATED APPLICATIONS

This application is a continuation of U.S. patent application Ser. No. 15/351,966, filed Nov. 15, 2016, which is a continuation-in-part of U.S. patent application Ser. No. 14/750,877, filed on Jun. 25, 2015 (now U.S. Pat. No. 9,549,969), which is a continuation of U.S. patent application Ser. No. 13/742,865, filed on Jan. 16, 2013, which is a continuation-in-part of U.S. patent application Ser. No. 13/371,076, filed on Feb. 10, 2012 (now U.S. Pat. No. 8,481,498), which claims priority to U.S. Provisional Application No. 61/587,420, filed on Jan. 17, 2012. U.S. patent application Ser. No. 13/742,865 also claims priority to U.S. Provisional Application No. 61/702,994, filed on Sep. 19, 2012. All of the applications mentioned in this paragraph are incorporated herein by reference in their entirety.

TECHNICAL FIELD

The present inventions relate generally to compositions, kits and methods for the reduction of cellular proliferation as, for example, in the treatment of cancer.

BACKGROUND

According to the U.S. National Cancer Institute's Surveillance Epidemiology and End Results (SEER) database for the year 2008, the most recent year for which incidence data are available, 11,958,000 Americans have invasive cancers. Cancer is the second most common cause of death in the United States, behind only heart disease, and accounts for one in four deaths. It has been estimated that approximately 1600 Americans die of cancer each day. In addition to the medical, emotional and psychological costs of cancer, cancer has significant financial costs to both the individual and society. It is estimated by the National Institutes of Health that the overall costs of cancer in 2010 was $263.8 billion. In addition, it is estimated that another $140.1 billion is lost in productivity due to premature death.

Cancer treatments today include surgery, hormone therapy, radiation, chemotherapy, immunotherapy, targeted therapy, and combinations thereof. Surgical removal of cancer has advanced significantly; however, there remains a high chance of recurrence of the disease. Hormone therapy using drugs such as aromatase inhibitors and luteinizing hormone-releasing hormone analogs and inhibitors has been relatively effective in treating prostate and breast cancers. Radiation and the related techniques of conformal proton beam radiation therapy, stereotactic radiosurgery, stereotactic radiation therapy, intraoperative radiation therapy, chemical modifiers, and radio sensitizers are effective at killing cancerous cells, but can also kill and alter surrounding normal tissue. Chemotherapy drugs such as aminopterin, cisplatin, methotrexate, doxorubicin, daunorubicin and others alone and in combinations are effective at killing cancer cells, often by altering the DNA replication process. Biological response modifier (BRM) therapy, biologic therapy, biotherapy, or immunotherapy alter cancer cell growth or influence the natural immune response, and involve administering biologic agents to a patient such as an interferons, interleukins, and other cytokines and antibodies such as rituximab and trastuzumab and even cancer vaccines such as Sipuleucel-T.

Recently, new targeted therapies have been developed to fight cancer. These targeted therapies differ from chemotherapy because chemotherapy works by killing both cancerous and normal cells, with greater effects on the cancerous cells. Targeted therapies work by influencing the processes that control growth, division, and the spread of cancer cells and signals that cause cancer cells to die naturally. One type of targeted therapy includes growth signal inhibitors such as trastuzumab, gefitinib, imatinib, centuximab, dasatinib and nilotinib. Another type of targeted therapy includes angiogenesis inhibitors such as bevacizumab that inhibit cancers from increasing surrounding vasculature and blood supply. A final type of targeted therapy includes apoptosis-inducing drugs that are able to induce direct cancer cell death.

Although all of these treatments have been effective to one degree or another, they all have drawbacks and limitations. In addition to many of the treatments being expensive, they also are often too imprecise or the cancers are able to adapt to them and become resistant.

Thus, there is a great need for additional cancer treatments. In particular, there is a need for treatments for cancers that have become resistant to other forms of treatment.

SUMMARY

The present invention provides compositions, combination therapies, kits, and methods for reducing undue cellular proliferation, including that associated with the treatment of cancer. In certain embodiments, the invention provides pharmaceutical compositions comprising at least one tyrosine hydroxylase inhibitor; at least one of melanin, a melanin promoter, or a combination thereof; at least one p450 3A4 promoter; at least one leucine aminopeptidase inhibitor; and, optionally, at least one growth hormone inhibitor. In other embodiments, the invention provides kits that comprise these components together with suitable packaging. Also provided are methods of reducing cellular proliferation and/or methods of treating cancer comprising administering an effective amount of at least one tyrosine hydroxylase inhibitor; at least one of melanin, a melanin promoter, or a combination thereof; at least one p450 3A4 promoter; at least one leucine aminopeptidase inhibitor; and, optionally, at least one growth hormone inhibitor to the subject in need thereof.

DETAILED DESCRIPTION OF ILLUSTRATIVE EMBODIMENTS

The present subject matter may be understood more readily by reference to the following detailed description which forms a part of this disclosure. It is to be understood that this invention is not limited to the specific products, methods, conditions or parameters described and/or shown herein, and that the terminology used herein is for the purpose of describing particular embodiments by way of example only and is not intended to be limiting of the claimed invention.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

As employed above and throughout the disclosure, the following terms and abbreviations, unless otherwise indicated, shall be understood to have the following meanings.

In the present disclosure the singular forms "a," "an," and "the" include the plural reference, and reference to a particular numerical value includes at least that particular value, unless the context clearly indicates otherwise. Thus, for example, a reference to "a compound" is a reference to one or more of such compounds and equivalents thereof known to those skilled in the art, and so forth. The term "plurality", as used herein, means more than one. When a range of values is expressed, another embodiment includes from the one particular and/or to the other particular value. Similarly, when values are expressed as approximations, by use of the antecedent "about," it is understood that the particular value forms another embodiment. All ranges are inclusive and combinable.

As used herein, the terms "component," "composition," "composition of compounds," "compound," "drug," "pharmacologically active agent," "active agent," "therapeutic," "therapy," "treatment," or "medicament" are used interchangeably herein to refer to a compound or compounds or composition of matter which, when administered to a subject (human or animal) induces a desired pharmacological and/or physiologic effect by local and/or systemic action.

As used herein, the terms "treatment" or "therapy" (as well as different forms thereof) include preventative (e.g., prophylactic), curative or palliative treatment. As used herein, the term "treating" includes alleviating or reducing at least one adverse or negative effect or symptom of a condition, disease or disorder. This condition, disease or disorder can be cancer.

As employed above and throughout the disclosure the term "effective amount" refers to an amount effective, at dosages, and for periods of time necessary, to achieve the desired result with respect to the treatment of the relevant disorder, condition, or side effect. It will be appreciated that the effective amount of components of the present invention will vary from patient to patient not only with the particular compound, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

"Pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

Within the present invention, the disclosed compounds may be prepared in the form of pharmaceutically acceptable salts. "Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein can be prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein that contain, for example, both amino and carboxy groups, also include reference to their corresponding zwitterions.

The term "stereoisomers" refers to compounds that have identical chemical constitution, but differ as regards the arrangement of the atoms or groups in space.

The term "administering" means either directly administering a compound or composition of the present invention, or administering a prodrug, derivative or analog which will form an equivalent amount of the active compound or substance within the body.

The terms "subject," "individual," and "patient" are used interchangeably herein, and refer to an animal, for example a human, to whom treatment, including prophylactic treatment, with the pharmaceutical composition according to the present invention, is provided. The term "subject" as used herein refers to human and non-human animals. The terms "non-human animals" and "non-human mammals" are used interchangeably herein and include all vertebrates, e.g., mammals, such as non-human primates, (particularly higher primates), sheep, dog, rodent, (e.g. mouse or rat), guinea pig, goat, pig, cat, rabbits, cows, horses and non-mammals such as reptiles, amphibians, chickens, and turkeys.

The term "inhibitor" as used herein includes compounds that inhibit the expression or activity of a protein, polypeptide or enzyme and does not necessarily mean complete inhibition of expression and/or activity. Rather, the inhibition includes inhibition of the expression and/or activity of a protein, polypeptide or enzyme to an extent, and for a time, sufficient to produce the desired effect.

The term "promoter" as used herein includes compounds that promote the expression or activity of a protein, polypeptide or enzyme and does not necessarily mean complete promotion of expression and/or activity. Rather, the promotion includes promotion of the expression and/or activity of a protein, polypeptide or enzyme to an extent, and for a time, sufficient to produce the desired effect.

In one embodiment, the present invention provides combination therapies that alter the defenses of cancerous cells to oxidative stress. One class of such therapies increases free radical availability to cancerous cells. A representative subclass of such therapies involves administration of pharmaceutical compositions comprising a tyrosine hydroxylase inhibitor, melanin or a melanin promoter, a p450 3A4 promoter, a leucine aminopeptidase inhibitor, and, optionally, a growth hormone inhibitor. Another subclass involves administration of pharmaceutical compositions comprising melanin and either a tyrosine hydroxylase inhibitor. Particular components of the pharmaceutical composition are described below.

While not intending to be bound by any particular mechanism of operation, tyrosine hydroxylase inhibitors according to the present invention function by accumulating in cancer cells and preventing them from forming a coating of either lipids or hyaluronan. By preventing the cancer cells from forming a coating of either lipids or hyaluron, the cancer cells are believed to be made more accessible to oxidative stress. Representative tyrosine hydroxylase inhibitors include tyrosine derivatives, which typically are rapidly absorbed by most cancers and inflamed tissues. Representative tyrosine derivatives include one or more of methyl (2R)-2-amino-3-(2-chloro-4-hydroxyphenyl) propanoate, D-tyrosine ethyl ester hydrochloride, methyl (2R)-2-amino-3-(2,6-dichloro-3,4-dimethoxyphenyl) propanoate H-D-Tyr (TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-$I_2$)—OSu, Fmoc-tyr(3-$NO_2$)—OH, and α-methyl-DL-tyrosine (also known as DL-2-Methyl-3-(4-Hydroxyphenyl) alanine).

The present invention involves the use of at least one of melanin, a melanin promoter, or a combination thereof. Thus, melanin can be used, one or more melanin promoters can be used, and both melanin and one or more melanin promoters can be used (either in separate dosage forms or in the same dosage form). Melanin promoters according to the present invention are chemical compounds that increase the production and/or the activity of melanin. Increased melanin levels are believed to reduce inflammation (through, for example, suppression of TNF) and exclude the sequestered lymph system. Melanin is a photo catalyst, and can therefore promote chemical reactions that generate free radicals which, in turn, can become accessible to cancer cells. Representative melanin promoters are methoxsalen and melanotan II.

In some instances, the tyrosine hydroxylase inhibitor is mixed with melanin in the same dosage form. This association of melanin with the tyrosine hydroxylase inhibitor is believed to facilitate uptake of melanin in cancer cells because tyrosine hydroxylase inhibitors are more readily taken up by such cells. In certain embodiments melanin is solubilized in a solubilizing agent and then mixed with the tyrosine hydroxylase inhibitor by methods known in the art. The solubilizing agent may be removed by standard techniques, such as evaporation, drying, etc. The solubilizing agent may be a non-toxic solubilizing agent, such as hydrogen peroxide or other solubilizing agents commonly known in the art. The melanin and/or the pharmaceutical composition may be further processed to optimize the pharmaceutical composition's effect on cancer cells. In another embodiment the pharmaceutical composition may include additional active agents and/or pharmaceutical excipients.

The pharmaceutical compositions of the invention also include a p450 3A4 promoter. "Cytochrome p450 3A4" (which can be abbreviated as "p450 3A4") is a member of the cytochrome p450 superfamily of enzymes, and is a mixed-function oxidase that is involved in the metabolism of xenobiotics in the body. It has the widest range of substrates of all of the cytochromes. The function of a p450 3A4 promoter in the pharmaceutical compositions of the invention is to increase the expression and/or the activity of p450 3A4. The increased p450 3A4 expression and/or activity is believed to reduce cortisone and estrogen levels in the patient. Additionally, the increased p450 3A4 expression and/or activity also slightly decreases blood pH, which is believed to help to preserve or enhance melanin activity. Representative p450 3A4 promoters are 5,5-diphenylhydantoin (sold commercially as, for example, Dilantin), valproic acid, and carbamazepine, which are believed to induce expression of the p450 3A4 enzyme.

The instant pharmaceutical compositions further include leucine aminopeptidase inhibitors (alternatively known as leucyl aminopeptidase inhibitors). Leucine aminopeptidases are enzymes that preferentially catalyze the hydrolysis of leucine residues at the N-terminus of peptides and/or proteins. Inhibiting the expression and/or activity of leucine aminopeptidases is believed to assist in tumor reabsorption by increasing cholesterol transport to the liver. Generally, it is believed that aminopeptidase inhibitors, including aminopeptidase inhibitors, deplete sensitive tumor cells of specific amino acids by preventing protein recycling, thus generating an antiproliferative effect. Representative leucine aminopeptidase inhibitors are N-[(2S,3R)-3-amino-2-hydroxy-4-phenylbutyryl]-L-leucine, and rapamycin.

The instant pharmaceutical compositions also optionally include a growth hormone inhibitor. Growth hormone (such as, for example, pancreatic growth hormone) induces cell replication. Inhibition of the expression and/or activity of growth hormone is believed to exclude normal cells from rapid replication while allowing cancer cells to continue to rapidly replicate and incorporate the tyrosine derivative. Representative growth hormone inhibitors are octreotide, somatostatin, and seglitide.

The pharmaceutical compositions of the invention can further include D-leucine. D-leucine is a stereoisomer of the naturally occurring L-leucine, the form of leucine incorporated into polypeptides and proteins. D-leucine cannot be incorporated into polypeptides and/or proteins. Along with the leucine aminopeptidase inhibitor, the D-leucine is believed to create a physiological environment that mimics a leucine shortage. Thus, the presence of D-leucine permits the use of lower doses of leucine aminopeptidase inhibitor in a pharmaceutical composition.

Also provided herein are kits including a combination therapy that creates alterations in the defenses of cancerous cells to oxidative stress. An intended suitable embodiment is a kit that includes a combination therapy that increases free radical availability to cancerous cells. Representative kits comprise a tyrosine hydroxylase inhibitor, melanin and/or a melanin promoter, a p450 3A4 promoter, a leucine aminopeptidase inhibitor and, optionally, a growth hormone inhibitor of the type described above, together with packaging for same. The kit can include one or more separate containers, dividers or compartments and, optionally, informational material such as instructions for administration. For example, each inhibitor or promoter (or the various combinations thereof) can be contained in a bottle, vial, or syringe, and the informational material can be contained in a plastic sleeve or packet or provided in a label. In some embodiments, the kit includes a plurality (e.g., a pack) of individual containers, each containing one or more unit dosage forms of a compound described herein. For example, the kit can include a plurality of syringes, ampules, foil packets, or blister packs, each containing a single unit dose of a compound described herein or any of the various combinations thereof. The containers of the kits can be air tight, waterproof (e.g., impermeable to changes in moisture or evaporation), and/or light-tight. The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device.

Methods of treating cancer in a subject also are provided, as are methods of reducing undue cellular proliferation. Such methods can include administering an effective amount of a combination therapy that creates alterations in the defenses of cancerous cells to oxidative stress. Representative methods of treating cancer include administering an effective amount of a combination therapy that increases free radical availability to cancerous cells. Suitable embodiments are methods that include administering an effective amount of the above-noted tyrosine hydroxylase inhibitor, melanin and/or melanin promoter, p450 3A4 promoter, leucine aminopeptidase inhibitor and, optionally, growth hormone inhibitor. Other suitable methods include administering an effective amount of melanin and a tyrosine hydroxylase inhibitor.

Suitable methods include simultaneous or at least contemporaneous administration of at least two of the tyrosine hydroxylase inhibitor, melanin or a melanin promoter, p450 3A4 promoter, and leucine aminopeptidase inhibitor, at least three of them, or each of them (in each case, optionally, with a growth hormone inhibitor). It is believed to be desirable that an effective concentration of these moieties be in the subject's bloodstream at the same time, and any dosing regimen that achieves this is within the scope of the present invention. The desired number of inhibitors and promoters can be provided in a single dosage form or any number of desired dosage forms, including in individual dosage forms. Representative dosage forms include tablets, capsules, caplets, sterile aqueous or organic solutions, reconstitutable powders, elixirs, liquids, colloidal or other types of suspensions, emulsions, beads, beadlets, granules, microparticles, nanoparticles, and combinations thereof. The amount of composition administered will, of course, be dependent on the subject being treated, the subject's weight, the severity of the condition being treated, the manner of administration, and the judgment of the prescribing physician.

Administration of the melanin, promoters, and/or inhibitors can be through various routes, including orally, nasally, subcutaneously, intravenously, intramuscularly, transdermally, vaginally, rectally or in any combination thereof. Transdermal administration can be effected using, for example, oleic acid, 1-methyl-2-pyrrolidone, or dodecylnonaoxyethylene glycol monoether.

The melanin, promoters and/or inhibitors can be administered during a cycle consisting of five to seven days of administering the melanin, promoters and/or inhibitors and one to two days of not administering the melanin, promoters and/or inhibitors. The melanin, promoters and/or inhibitors can be administered over the course of at least six of said cycles. It can be desirable to administer these components about two hours between meals to facilitate uptake.

The subject to which the instant compositions are administered can be a mammal, preferably a human.

In one representative method, 60 mg of the tyrosine derivative is administered orally and 0.25 mL of a 2 mg/mL suspension of the tyrosine derivative is administered subcutaneously; 10 mg of the methoxsalen is administered orally and 0.25 mL of a 1 mg/mL suspension of the methoxsalen is administered subcutaneously; 30 mg of the 5,5-diphenylhydantoin is administered orally; and 20 mg of the N-[(2S,3R)-3-amino-2-hydroxy-4-phenylbutyryl]-L-leucine is administered orally.

In certain embodiments, the combination therapy comprises: (i) a dosage form containing melanin (50 mcg) and α-methyl-DL-tyrosine (75 mg); (ii) a dosage form containing 5,5-diphenylhydantoin (15 mg) and α-methyl-DL-tyrosine (75 mg); (iii) a dosage form containing 3-amino-2-hydroxy-4-phenylbutyryl]-L-leucine (50 mcg) and α-methyl-DL-tyrosine (75 mg); (iv) a dosage form containing 3-amino-2-hydroxy-4-phenylbutyryl]-L-leucine (5 mcg), melanotan II (10 mcg), and 5,5-diphenylhydantoin (2 mg); and (v) a dosage form containing α-methyl-DL-tyrosine (5 mg) in NaCl bacteriostatic water. In other embodiments, the combination therapy comprises: (i) a dosage form containing melanin (50 mcg) and α-methyl-DL-tyrosine (75 mg); (ii) a dosage form containing 5,5-diphenylhydantoin (15 mg) and α-methyl-DL-tyrosine (75 mg); (iii) a dosage form containing rapamycin (0.2 mg) and α-methyl-DL-tyrosine (75 mg); (iv) a dosage form containing rapamycin (0.15 mcg), melanotan II (10 mcg), and 5,5-diphenylhydantoin (2 mg); and (v) a dosage form containing α-methyl-DL-tyrosine (5 mg) in NaCl bacteriostatic water. Dosages that are two times greater than this, and even four times greater than this, are believed to be both safe and efficacious.

Representative methods include those in which the cancer is non-small cell lung cancer. In certain embodiments, the non-small cell lung cancer is stage IV non-small cell lung cancer. In yet other embodiments, the cancer is ovarian cancer, breast cancer, cervical cancer, pancreatic cancer, stomach cancer, brain cancer, liver cancer, testicular cancer, leukemia, lymphoma, appendix cancer, biliary cancer, choleangiocarcinoma, colon cancer, colorectal cancer, germ cell tumor, glioma, Hodgkin's lymphoma, lung cancer, neuroblastoma, prostate cancer, renal cancer, sarcoma, thyroid cancer, tongue cancer, tonsil squamous cell carcinoma, or urothelial cancer.

In certain embodiments, one or more of the tyrosine hydroxylase inhibitor; the melanin promoter; the p450 3A4 promoter; and the leucine aminopeptidase inhibitor is a nucleic acid, protein, antibody or antigen-binding fragment of an antibody.

The present methods can include not only the disclosed administration step but also the step of assessing progression of said cancer in said subject and/or the extent of cellular proliferation. The assessing step can be performed before or after the administering step.

Suitable embodiments can include a pharmaceutical composition comprising a tyrosine hydroxylase inhibitor, melanin and/or a melanin promoter, a p450 3A4 promoter, and a leucine aminopeptidase inhibitor. The pharmaceutical composition can further comprise a growth hormone inhibitor. The growth hormone can be pancreatic growth hormone. The growth hormone inhibitor can be octreotide or somatostatin. The tyrosine hydroxylase inhibitor can be a tyrosine derivative. The tyrosine derivative can be one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I$_2$)—OSu, Fmoc-tyr(3-NO$_2$)—OH, and α-methyl-DL-tyrosine. The melanin promoter can be methoxsalen or melanotan II. The p450 3A4 promoter can be 5,5-diphenylhydantoin. The p450 3A4 promoter can be valproic acid or carbamazepine. The leucine aminopeptidase inhibitor can be N-[(2S,3R)-3-amino-2-hydroxy-4-phenylbutyryl]-L-leucine or rapamycin. The pharmaceutical compositions of the invention can further comprise D-leucine.

Also provided herein are kits comprising a tyrosine hydroxylase inhibitor, melanin and/or a melanin promoter, a p450 3A4 promoter, and a leucine aminopeptidase inhibitor, together with packaging for same. The kit can further comprise a growth hormone inhibitor. The growth hormone can be pancreatic growth hormone. The growth hormone inhibitor can be octreotide or somatostatin. The tyrosine hydroxylase inhibitor can be a tyrosine derivative. The tyrosine derivative can be one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I$_2$)—OSu, Fmoc-tyr(3-NO$_2$)—OH, and α-methyl-DL-tyrosine. The melanin promoter can be methoxsalen or melanotan II. The p450 3A4 promoter can be 5,5-diphenylhydantoin, valproic acid or carbamazepine. The leucine aminopeptidase inhibitor can be N-[(2S,3R)-3-amino-2-hydroxy-4-phenylbutyryl]-L-leucine or rapamycin. The kits of the invention can further comprise D-leucine.

Methods of treating cancer in a subject are also provided comprising administering an effective amount of a tyrosine hydroxylase inhibitor, melanin and/or a melanin promoter, a p450 3A4 promoter, and a leucine aminopeptidase inhibitor to the subject in need thereof. In a suitable embodiment, the method of treating cancer can further comprise a growth hormone inhibitor. In certain embodiments, at least two of the components (i.e., melanin, promoters and/or inhibitors) are administered simultaneously. In other embodiments, at least three of the components are administered simultaneously. Each of the components can be administered simultaneously. In suitable embodiments, the components are administered orally, subcutaneously, intravenously, transdermally, vaginally, rectally or in any combination thereof. The transdermal administration can be done with oleic acid, 1-methyl-2-pyrrolidone, or dodecylnonaoxyethylene glycol monoether. In other embodiments, the components are administered during a cycle consisting of five to seven days of administering the components and one to two days of not administering the components. The components can be administered over the course of at least six of said cycles. The tyrosine hydroxylase inhibitor can be a tyrosine derivative. The tyrosine derivative can be one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr (TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I$_2$)—OSu, Fmoc-tyr(3-NO$_2$)—OH, and α-methyl-DL-tyrosine. In a suitable embodiment of the method, 60 mg of the tyrosine derivative is administered orally and 0.25 mL of a 2 mg/mL suspension of the tyrosine derivative is administered subcutaneously. The melanin promoter can be methoxsalen. In another suitable method, 10 mg of the methoxsalen is administered orally and 0.25 mL of a 1 mg/mL suspension of the methoxsalen is administered subcutaneously. The melanin promoter can also be melanotan II. The p450 3A4 promoter can be 5,5-diphenylhydantoin. In another suitable method, 30 mg of the 5,5-diphenylhydantoin is administered orally. The p450 3A4 promoter can also be valproic acid or carbamazepine. The leucine aminopeptidase inhibitor can be N-[(2S,3R)-3-amino-2-hydroxy-4-phenylbutyryl]-L-leucine. In another suitable method, 20 mg of the N-[(2S,3R)-3-amino-2-hydroxy-4-phenylbutyryl]-L-leucine is administered orally. The leucine aminopeptidase inhibitor can also be rapamycin. The growth hormone can be pancreatic growth hormone. The growth hormone inhibitor can be octreotide. The method can further comprise administering an effective amount of D-leucine. The subject can be a mammal and that mammal can be a human. Representative methods include those in which the cancer is non-small cell lung cancer. In certain embodiments, the non-small cell lung cancer is stage IV non-small cell lung cancer. In other embodiments, the cancer is ovarian cancer, breast cancer, cervical cancer, pancreatic cancer, stomach cancer, brain cancer, liver cancer, testicular cancer, leukemia, lymphoma, appendix cancer, biliary cancer, choleangiocarcinoma, colon cancer, colorectal cancer, germ cell tumor, glioma, Hodgkin's lymphoma, lung cancer, neuroblastoma, prostate cancer, renal cancer, sarcoma, thyroid cancer, tongue cancer, tonsil squamous cell carcinoma, or urothelial cancer. In other suitable embodiments, the tyrosine hydroxylase inhibitor, the melanin promoter, the p450 3A4 promoter, and the leucine aminopeptidase inhibitor is one or more of a nucleic acid, protein, antibody or antigen-binding fragment of an antibody. Another suitable embodiment further comprises assessing progression of said cancer in said subject. The assessing step can be performed before said administering step or the assessing step can be performed after said administering step.

Methods of reducing cell proliferation in a subject are also provided comprising administering an effective amount of a tyrosine hydroxylase inhibitor; melanin and/or a melanin promoter; a p450 3A4 promoter; and a leucine aminopeptidase inhibitor to the subject in need thereof. In a suitable embodiment, the method of treating cancer can further comprise a growth hormone inhibitor. In certain embodiments, at least two of the components (i.e., melanin, promoters and/or inhibitors) are administered simultaneously. In other embodiments, at least three of the components are administered simultaneously. Each of the components can be administered simultaneously. In suitable embodiments, components are administered orally, subcutaneously, intravenously, transdermally, vaginally, rectally or in any combination thereof. The transdermal administration can be done with oleic acid, 1-methyl-2-pyrrolidone, or dodecylnonaoxyethylene glycol monoether. In other embodiments, the components are administered during a cycle consisting of five to seven days of administering the components and one to two days of not administering the components. The components can be administered over the course of at least six of said cycles. The tyrosine hydroxylase inhibitor can be a tyrosine derivative. The tyrosine derivative can be one or more of methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OME HCl, H-3,5-diiodo-tyr-OME HCl, H-D-3,5-diiodo-tyr-OME HCl, H-D-tyr-OME HCl, D-tyrosine methyl ester hydrochloride, D-tyrosine-ome HCl, methyl D-tyrosinate hydrochloride, H-D-tyr-OMe-HCl, D-tyrosine methyl ester HCl, H-D-Tyr-OMe-HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr (3,5-I$_2$)—OSu, Fmoc-tyr(3-NO$_2$)—OH, and α-methyl-DL-tyrosine. In a suitable embodiment of the method, 60 mg of the tyrosine derivative is administered orally and 0.25 mL of a 2 mg/mL suspension of the tyrosine derivative is administered subcutaneously. The melanin promoter can be methoxsalen. In another suitable method, 10 mg of the methoxsalen is administered orally and 0.25 mL of a 1 mg/mL suspension of the methoxsalen is administered subcutaneously. The melanin promoter can also be melanotan II. The p450 3A4 promoter can be 5,5-diphenylhydantoin. In another suitable method, 30 mg of the 5,5-diphenylhydantoin is administered orally. The p450 3A4 promoter can also be valproic acid or carbamazepine. The leucine aminopeptidase inhibitor can be N-[(2S,3R)-3-amino-2-hydroxy-4-phenylbutyryl]-L-leucine. In another suitable method, 20 mg of the N-[(2S,3R)-3-amino-2-hydroxy-4-phenylbutyryl]-L-leucine is administered orally. The leucine aminopeptidase inhibitor can also be rapamycin. The growth hormone can be pancreatic growth hormone. The growth hormone inhibitor can be octreotide. The method can further comprise administering an effective amount of D-leucine. The subject can be a mammal and the mammal can be a human. Representative methods include those in which the cancer is non-small cell lung cancer. In certain embodiments, the non-small cell lung cancer is stage IV non-small cell lung cancer. In other embodiments, the cancer is ovarian cancer, breast cancer, cervical cancer, pancreatic cancer, stomach cancer, brain cancer, liver cancer, testicular cancer, leukemia, lymphoma, appendix cancer, biliary cancer, choleangiocarcinoma, colon cancer, colorectal cancer, germ cell tumor, glioma, Hodgkin's lymphoma, lung cancer, neuroblastoma, prostate cancer, renal cancer, sarcoma, thyroid cancer, tongue cancer, tonsil squamous cell carcinoma, or urothelial cancer. In other suitable embodiments, the tyrosine hydroxylase inhibitor, the melanin promoter, the p450 3A4 promoter, and the leucine aminopeptidase inhibitor is one or more of a nucleic acid, protein, antibody or antigen-binding fragment of an antibody. Another suitable embodiment further comprises assessing progression of said cancer in said subject. The assessing step can be performed before said administering step or the assessing step can be performed after said administering step.

The following examples of specific embodiments for carrying out the present invention are offered for illustrative purposes only, and are not intended to limit the scope of the present invention in any way.

Representative methods of administration of the pharmaceutical compositions and combination therapies also are provided. Various embodiments of the present invention further relate to methods of administering a pharmaceutical composition or combination therapy to a human patient for the treatment of cancer. The methods may comprise administering a pharmaceutical composition or combination therapy by generally accepted routes of administration (e.g., oral, subcutaneous, parenteral, inhalation, topical, etc.). In some instances, a pharmaceutical composition or combination therapy may be administered orally and/or subcutaneously. In some instances, a pharmaceutical composition or combination therapy may be administered to human patients between meals.

In certain embodiments of the present invention, a pharmaceutical composition or combination therapy may be administered to a human patient for 5 days per week for a period of 6 weeks, creating one cycle of 30 days of treatment. Depending on the outcome after 6 weeks or one cycle of treatment, additional cycles of the pharmaceutical composition or combination therapy may be administered.

The present invention also provides:
  pharmaceutical compositions comprising a tyrosine hydroxylase inhibitor; and melanin, a melanin promoter, or a combination thereof (preferably melanin);
  pharmaceutical compositions comprising a tyrosine hydroxylase inhibitor and a p450 3A4 promoter;
  pharmaceutical compositions comprising a tyrosine hydroxylase inhibitor and a leucine aminopeptidase inhibitor; and
  pharmaceutical compositions comprising melanin, a melanin promoter, or a combination thereof (preferably melanotan II); a p450 3A4 promoter; and a leucine aminopeptidase inhibitor.

The tyrosine hydroxylase inhibitor in such compositions preferably is α-methyl-DL-tyrosine, the p450 3A4 promoter preferably is 5,5-diphenylhydantoin, and the leucine aminopeptidase inhibitor preferably is N-[(2S,3R)-3-amino-2-hydroxy-4-phenylbutyryl]-L-leucine. The invention also provides kits comprising each of these pharmaceutical compositions, along with a pharmaceutical composition comprising a tyrosine hydroxylase inhibitor; as well as methods comprising administering each of the pharmaceutical compositions to a patient along with a pharmaceutical composition comprising a tyrosine hydroxylase inhibitor, preferably such that they are administered to the patient within a 24 hour period.

Example 1

A clinical study was performed to evaluate the effectiveness, safety, acceptability, and tolerability of a combination therapy in accordance with embodiments of the present invention as a treatment for metastatic cancer.

The combination therapy comprised the following:
(a) capsule containing melanin (50 mcg) and α-methyl-DL-tyrosine (75 mg), administered orally;
(b) capsule containing 5,5-diphenylhydantoin (15 mg) and α-methyl-DL-tyrosine (75 mg), administered orally;
(c) capsule containing 5,5-diphenylhydantoin (15 mg) and α-methyl-DL-tyrosine (75 mg), administered orally;
(d) capsule containing rapamycin (0.2 mg) and α-methyl-DL-tyrosine (75 mg), administered orally;
(e) suspension containing rapamycin (0.15 mcg), melanotan II (10 mcg), and 5,5-diphenylhydantoin (2 mg), administered subcutaneously; and
(f) suspension containing α-methyl-DL-tyrosine (5 mg) in NaCl bacteriostatic water, administered subcutaneously.

Each patient was administered the combination therapy five days per week for six weeks. More than 200 patients were screened. The criteria included patients with any metastatic cancer. Thirty patients meeting the criteria were accepted and participated in the study.

Treatment of Metastatic Breast Cancer

Fourteen patients in the study suffered from metastatic breast cancer. Patient information and results are as follows in Table 1:

TABLE 1

| Patient Characteristics | |
|---|---|
| Average age | 55 (40-70 years old) |
| Female | 14/14 |
| Caucasian | 13/14 |
| Prior to Study | |
| Declined routine treatment prior to study enrollment | 4/14 |
| Used all available treatment and were considered incurable | 10/14 |
| Treatment Results | |
| 1-3 point improvement in ECOG rating | 11/14 |
| 1-5 point improvement in EORTC rating (scale 1-7) | 10/14 |
| Weight | |
| Gained weight | 4/14 (1-5 lbs) |
| Remained the same weight | 6/14 |
| Lost weight | 4/14 (1-2 lbs) |
| Pain | |
| Reduction in pain level (scale of 1-10) | 8/14 (1-9) |
| Entered study with no pain and maintained the same level | 6/14 |
| Entered study on pain medication | 6/14 |
| No longer needed pain medication at the end of the cycle | 5/6 |
| Evidence of Cancer | |
| Disease free with normal physical exam, review of systems, and imaging | 3/14 |
| Significant reduction in quantity and/or size of the largest tumor | 5/14 |
| Reduction in quantity and/or size of the largest tumor | 2/14 |
| No progression of the cancer | 4/14 |

TABLE 1-continued

Survival

| | |
|---|---|
| Alive | 14/14 |
| 33-37 wks | 4/14 |
| 27-29 wks | 5/14 |
| 12-19 wks | 5/14 |
| Current Status | |
| Went home | 3/14 |
| Continued treatment | 11/14 |

One side effect of the therapy was hyperpigmentation in all of the patients. Overall, all of the patients tolerated the combination therapy and no adverse events were reported.

Over 200 cancer patients were screened in a clinical trial. Thirty (30) subjects meeting the study criteria consented. The average patient age was 56 years old with a range of 30 years old to 70 years old. The patients in the study were administered a treatment regimen that included a tyrosine hydroxylase inhibitor (i.e., α-methyl-DL tyrosine), a melanin promoter (i.e., melanotan II), a p450 3A4 promoter (i.e., 5,5-diphenylhydantoin), and a leucine aminopeptidase inhibitor (i.e., rapamycin). These compounds were administered on each of five days per week for a period of six weeks, with one or two days off between weekly cycles.

After six weeks of treatment, 12 of the 30 patients (40%) maintained the same rating under the Eastern Cooperative Oncology Group (ECOG) 0-5 scale (see Oken, et al., Toxicity And Response Criteria Of The Eastern Cooperative Oncology Group, Am. J. Clin. Oncol., 5:649-655, 1982). Fourteen (14) of 30 (46%) had 1-3 point improvement in their ECOG rating.

Fourteen (14) of the 30 patients (46%) maintained the same rating under the European Organisation for the Research and Treatment of Cancer Quality of Life Questionnaire Core (EORTC) 1-7 scale (see, e.g., Bergman, et al., The EORTC QLQ-LC13: a modular supplement to the EORTC Core Quality of Life Questionnaire (QLQ-C30) for use in lung cancer clinical trials, EORTC Study Group on Quality of Life, Eur. J. Cancer, 1994. 30A(5): p. 635-42). Sixteen (16) of 30 (54%) had 1-5 point improvement in their EORTC rating.

Eleven (11) of the 30 patients gained weight of 1 to 9 pounds, 17 of 30 stayed the same weight, and 2 of 30 lost 1 to 2 pounds.

Thirteen (13) of 30 (43%) had a reduction in pain levels. Seventeen (17) of 30 (57%) entered with minimal pain and maintained the same level. Nine (9) of 30 (30%) entered the study on pain medication and 8 of those nine (89%) no longer needed pain medication at the end of the cycle.

No disease was detected in four (4) of 30 (13%) with normal physical exam, review of systems, and imaging. Eight (8) of 30 (27%) had significant reduction in quantity of tumors and/or size of the largest tumor. Eight (8) of 30 (27%) exhibited reduction in quantity of tumors and/or size of the largest tumor. Ten (10) of 30 (33%) showed no progression of disease.

Twenty nine (29) of the 30 patients were alive with median survival of 22 weeks. Thirteen (13) of 30 (43%) were released and went home. Seventeen (17) of 30 (57%) continue with the treatment. All of the subjects developed hyperpigmentation.

Overall, the above-noted treatment was well tolerated by the subjects, with no adverse events related to the treatment, and responses have been documented to the treatment 100%.

Example 2

In one aspect, the present invention provides methods of inducing melanin production in vivo with one or both of methoxsalen and melanotan and/or through administration of melanin. Without intending to be bound by any particular theory of operation, melanin is believed to be beneficial because of its photocatalytic nature and its ability to convert various wavelengths of ambient or induced electromagnetic radiation into electrical energy, thus potentiating desirable reactions or dislocations. In some patients, either because of genetic variation, infirmity, necessity of expedited availability, or to realize maximum effectiveness, it has been determined that melanin preferably is combined mechanically or chemically with α-methyl-DL-tyrosine prior to administration.

Melanin as a photocatalyst is believed to have polarity at points in its physical mass. It has been determined that small melanin particles may produce less electrical energy than larger particles, and a plurality of melanin particles tend not to accumulate in polarity-specific formations. An effective method to obtain high yield of electrical energy from melanin is to form the melanin in large, polarized particles. By implication, it is believed that nanoparticles, regardless of quantity, are not as desirable as larger particles for cancer treatment, and that larger particles have a greater capacity to be accepted by cancer cell membranes.

In accordance with certain embodiments, melanin is combined with α-methyl-DL-tyrosine in at least three ways.

1) Melanin, either naturally occurring or synthetic, is mechanically mixed with compressive force to adhere the melanin, which is non-water soluble and somewhat malleable, with the α-methyl-DL-tyrosine. Following the initial combining of these components, it is desirable to add additional α-methyl-DL-tyrosine until substantial coverage of the melanin is achieved.

2) Melanin can be solubilized by many methods as described in U.S. Pat. No. 5,225,435, the contents of which are incorporated herein by reference. One preferred method involves mixing melanin with distilled water and hydrogen peroxide to achieve a melanin concentration of at least 5 weight percent, and then placing the resulting composition in a microwave oven until it reaches a boiling point. The dissolved melanin that is produced is used to infuse or saturate through the mass of α-methyl-DL-tyrosine. The composition is then dried and the dry powder is used.

3) α-Methyl-DL-tyrosine is placed in distilled water with 5-benzyloxy-6-methoxy-indole and sealed for up to a month. The L portion of the racemic α-methyl-DL-tyrosine is believed to convert to (DOPA) melanin. The size of the melanin particle can be controlled by controlling the time of growth period. The powder produced is then cleaned and dried. The ratio of the racemic mix is no longer 50/50, but the utility of the chemically combined ingredients facilitates penetration of the melanin even with reduced L component and appears to offer potentially sufficient benefit.

What is claimed:

1. A method for treating cancer in a patient comprising administering to the patient an effective amount of:
   a) a tyrosine hydroxylase inhibitor that is methyl (2R)-2-amino-3-(2-chloro-4 hydroxyphenyl) propanoate, D-tyrosine ethyl ester hydrochloride, methyl (2R)-2-amino-3-(2,6-dichloro-3,4-dimethoxyphenyl) propanoate H-D-Tyr(TBU)-allyl ester HCl, methyl (2R)-2-amino-3-(3-chloro-4,5-dimethoxyphenyl) propanoate, methyl (2R)-2-amino-3-(2-chloro-3-hydroxy-4-methoxyphenyl) propanoate, methyl (2R)-2-amino-3-

(4-[(2-chloro-6-fluorophenyl) methoxy] phenyl) propanoate, methyl (2R)-2-amino-3-(2-chloro-3,4-dimethoxyphenyl) propanoate, methyl (2R)-2-amino-3-(3-chloro-5-fluoro-4-hydroxyphenyl) propanoate, diethyl 2-(acetylamino)-2-(4-[(2-chloro-6-fluorobenzyl) oxy] benzyl malonate, methyl (2R)-2-amino-3-(3-chloro-4-methoxyphenyl) propanoate, methyl (2R)-2-amino-3-(3-chloro-4-hydroxy-5-methoxyphenyl) propanoate, methyl (2R)-2-amino-3-(2,6-dichloro-3-hydroxy-4-methoxyphenyl) propanoate, methyl (2R)-2-amino-3-(3-chloro-4-hydroxyphenyl) propanoate, H-DL-tyr-OMe HCl, H-3,5-diiodo-tyr-OMe HCl, H-D-3,5-diiodo-tyr-OMe HCl, H-D-tyr-OMe HCl, (2R)-2-amino-3-(4-hydroxyphenyl) propionic acid, (2R)-2-amino-3-(4-hydroxyphenyl) methyl ester hydrochloride, methyl (2R)-2-amino-3-(4-hydroxyphenyl) propanoate hydrochloride, methyl (2R)-2-azanyl-3-(4-hydroxyphenyl) propanoate hydrochloride, 3-chloro-L-tyrosine, 3-nitro-L-tyrosine, 3-nitro-L-tyrosine ethyl ester hydrochloride, DL-m-tyrosine, DL-o-tyrosine, Boc-Tyr(3,5I$_2$)-OSu, Fmoc-tyr(3-NO$_2$)—OH, and α-methyl-DL-tyrosine;

b) melanin, a melanin promoter that is methoxsalen or melanotan II, or a combination of melanin, methoxsalen and melanotan II;

c) a p450 3A4 promoter that is 5,5-diphenylhydantoin, valproic acid, or carbamazepine; and d) a leucine aminopeptidase inhibitor that is N-[(2S,3R)-3-amino-2-hydroxy-4-phenylbutyryl]-L-leucine, or rapamycin; and wherein said cancer is metastatic cancer.

2. The method of claim 1, wherein each of said tyrosine hydroxylase inhibitor, said melanin, melanin promoter, or combination of melanin, methoxsalen and melanotan II; said p450 3A4 promoter; and said leucine aminopeptidase inhibitor is administered to said patient within a 24 hour period.

3. The method of claim 1, wherein each of said tyrosine hydroxylase inhibitor, said melanin, melanin promoter, or combination of melanin, methoxsalen and melanotan II; said p450 3A4 promoter; and said leucine aminopeptidase inhibitor_is administered to said patient five days per week for six weeks.

4. The method of claim 1, wherein said tyrosine hydroxylase inhibitor is α-methyl-DL-tyrosine.

\* \* \* \* \*